(12) United States Patent
Johanson (10) Patent No.: US 6,845,890 B2
(45) Date of Patent: Jan. 25, 2005

(54) BULK GRANULAR SOLIDS GRAVITY FLOW CURING VESSEL

(75) Inventor: Jerry R. Johanson, San Luis Obispo, CA (US)

(73) Assignee: Universal Aggregates, LLC, South Park, PA (US)

(*) Notice: Subject to any disclaimer, the term of this patent is extended or adjusted under 35 U.S.C. 154(b) by 155 days.

(21) Appl. No.: 10/122,830

(22) Filed: Apr. 15, 2002

(65) Prior Publication Data

US 2003/0071090 A1 Apr. 17, 2003

Related U.S. Application Data

(60) Provisional application No. 60/329,898, filed on Oct. 16, 2001.

(51) Int. Cl.⁷ ............................................... B65D 83/00
(52) U.S. Cl. ..................... 222/459; 222/547; 366/341
(58) Field of Search ............................ 222/185.1, 459, 222/547, 564, 460; 366/341

(56) References Cited

U.S. PATENT DOCUMENTS

| | | |
|---|---|---|
| 1,542,380 A | 6/1925 | Foster |
| 3,081,009 A | 3/1963 | Cooper |
| 3,985,244 A | 10/1976 | Gessler et al. |
| 3,995,753 A | 12/1976 | Millar et al. |
| 4,958,741 A | 9/1990 | Johanson |
| 5,361,945 A | 11/1994 | Johanson |
| 5,462,351 A | 10/1995 | Royal |
| 5,617,975 A | 4/1997 | Johanson et al. |
| 5,778,558 A | 7/1998 | Wenger et al. |
| 6,055,781 A | 5/2000 | Johanson |
| 6,086,307 A | 7/2000 | Johanson |
| 6,089,417 A | 7/2000 | Snekkenes et al. |
| 6,139,241 A | 10/2000 | Craig et al. |
| 6,250,514 B1 | 6/2001 | Hansson |
| 6,280,575 B1 | 8/2001 | Prough et al. |
| 6,336,573 B1 | 1/2002 | Johanson |

Primary Examiner—Philippe Derakshani
(74) Attorney, Agent, or Firm—Robert F. Lenart, Esq.; Pietragallo, Bosick & Gordon (57) ABSTRACT

A bulk granular solids gravity flow curing vessel comprises an upper curing unit having a top opening for receiving particulate solids, a lower curing unit coupled to receive particulate solids from the upper curing unit, and at least one of the upper and lower curing units including a first intermediate section having substantially vertical sidewalls, a first hopper positioned to receive the particulate solids from the intermediate section, and a first velocity adjustment means positioned in the intermediate section and/or the first hopper. A bulk granular solids gravity flow curing vessel comprising a first section having substantially vertical sidewalls, a first hopper positioned to receive particulate solids from the first section, and a first velocity adjustment means positioned in the first section is also described. A bulk granular solids gravity flow curing vessels comprising a first section having substantially vertical sidewalls, a first velocity adjustment means positioned in the first section and having non-vertical sidewalls, a second section having non-vertical sidewalls, second velocity adjustment means positioned in the second section and having substantially vertical sidewalls is further described.

39 Claims, 10 Drawing Sheets

BULK GRANULAR SOLIDS GRAVITY FLOW CURING VESSEL

CROSS REFERENCE TO RELATED PATENT APPLICATION

This application claims the benefit of U.S. Provisional Application 60/329,898, filed Oct. 16, 2001.

BACKGROUND INFORMATION

When bulk granular solids, such as aggregates, sugars, salts, chlorine compounds, polymers, or other materials that contain liquid soluble or reactive components are formed, they often tend to stick together. To prevent this sticking, the bulk solids are exposed to a curing atmosphere for several minutes or hours to condition the surface of the granules. This process usually requires storage in a confined space so as to control the curing conditions. A curing vessel is ideal for such curing provided that there is some slight inter-particle motion during the curing time to prevent sticking. A curing vessel is most efficient if the retention time of particles entering the vessel at the same time is about the same for all the particles. Inter-particle motion is difficult to maintain in a batch process, and the most efficient methods use a continuous moving bed process.

Current methods for curing bulk granular solids include belt, vibratory, and screw conveyors, and various mixers such as tumble blenders, rotary cylinders, ribbon blenders, and plow blenders. All these tend to degrade the particles and produce fines. They also have limited low production rates. The most effective, most energy efficient, least particle degrading, high capacity curing vessel is one using continuous gravity flow of a contact bed. Current designs for contact bed gravity flow vessels neglect one or more of the following preferred conditions: (a) bulk solids contact pressure is preferably kept below the crushing pressure for the particles; (b) inter-particle motion between particles preferably occurs sufficiently to keep the particles from sticking; (c) retention time of the vessel is preferably about the same for all the particles; and (d) there are preferably no non-flowing regions in the vessel.

There is a need for a bulk solids curing vessel that can be configured to address these preferred conditions.

SUMMARY OF THE INVENTION

A bulk granular solids gravity flow curing vessel comprises an upper curing unit having a top opening for receiving particulate solids, a lower curing unit coupled to receive particulate solids from the upper curing unit, and at least one of the upper and lower curing units including a first intermediate section having substantially vertical sidewalls, a first hopper positioned to receive the particulate solids from the intermediate section, and a first velocity adjustment means positioned in the intermediate section and/or the first hopper.

At least one of the upper and lower curing units can include a conical bin, wherein the first velocity adjustment means comprises a central insert positioned along a central axis of the bin. The central insert can comprise a rod positioned along the central axis of the bin, and a plurality of plates spaced along the rod and lying in planes that are perpendicular to the axis. The central insert can further comprise a plurality of cones and/or cylinders, each of the cones and/or cylinders having a base positioned adjacent to one of the plates.

A second one of the upper and lower curing units can include a second intermediate section having substantially vertical sidewalls, a second hopper positioned to receive the particulate solids from the intermediate section, and a second velocity adjustment means positioned in the intermediate section and/or the first hopper. The second velocity adjustment insert can include a hollow cylinder that can be positioned to extend into the second hopper. The diameter of the hollow cylinder can be approximately one half of the diameter of the second intermediate section.

The second velocity adjustment insert can alternatively comprise a horizontal flat plat. The second velocity adjustment insert can further comprise an upper extension and/or a lower extension.

The first velocity adjustment means can comprise a central insert positioned along a central axis of the upper curing unit. The upper curing unit can comprise a frusto-conical bin. The central insert can comprise a rod positioned along the central axis of the bin, and a plurality of plates spaced along the rod and lying in planes that are perpendicular to the central axis. The central insert can further comprise a plurality of cones and/or cylinders, each of the cones and/or cylinders having a base positioned adjacent to one of the plates. The upper curing unit can alternatively comprise a plurality of frustum and cylindrical sections.

A second velocity adjustment insert can be positioned in the lower curing unit. The second velocity adjustment insert can comprise a hollow cylinder or a horizontal flat plat. Upper and lower extensions can be connected to the plate.

The upper curing unit can comprise one or more conical sections having a convergence angle of less than 10 degrees from vertical. The first hopper can comprise a one-dimensional converge racetrack hopper. A plurality of additional one-dimensional converge racetrack hoppers can be coupled to the first hopper. A vertically adjustable cylinder can coupled to the bottom of each of the one-dimensional converge racetrack hoppers.

The invention also encompasses bulk granular solids gravity flow curing vessels comprising a first section having substantially vertical sidewalls, a first hopper positioned to receive particulate solids from the first section, and a first velocity adjustment means positioned in the first section.

The invention further encompasses bulk granular solids gravity flow curing vessels comprising a first section having substantially vertical sidewalls, a first velocity adjustment means positioned in the first section and having non-vertical sidewalls, a second section having non-vertical sidewalls, second velocity adjustment means positioned in the second section and having substantially vertical sidewalls.

DETAILED DESCRIPTION OF THE INVENTION

This invention provides a bulk solids vessel comprising an essentially vertical upper and converging lower section that limits solids contact pressure on bulk granular solids passing through it to less than the bulk crushing pressure of the granules and provides a means for introducing inter-particle motion sufficient to prevent particle sticking. The difference in retention time of any two particles introduced into the vessel is generally within plus or minus approximately 30% of the average retention time of all the particles in the vessel, and the vessel wall can be steep enough and of such a shape that there are no non-flowing regions in the vessel.

Figure 1A:
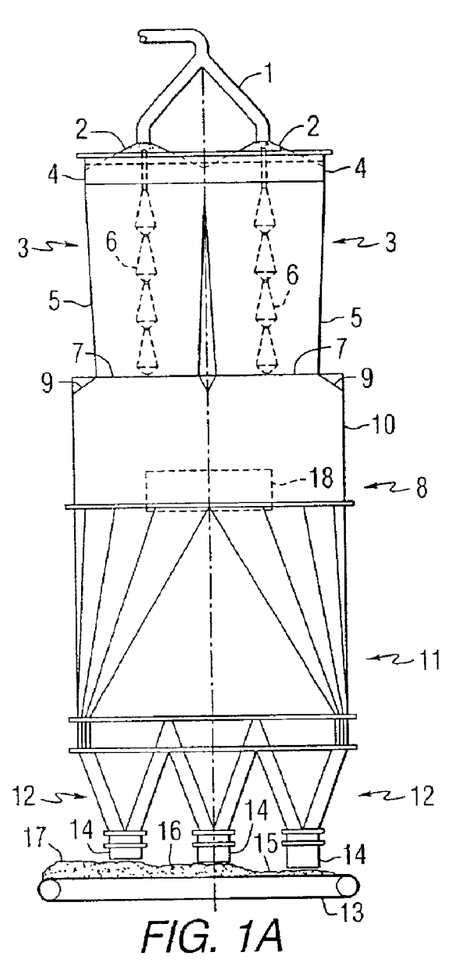
FIGS. 1A, 1B and 1C are front, side and top views of a curing vessel constructed in accordance with an embodiment of the present invention.
Figure 1B:
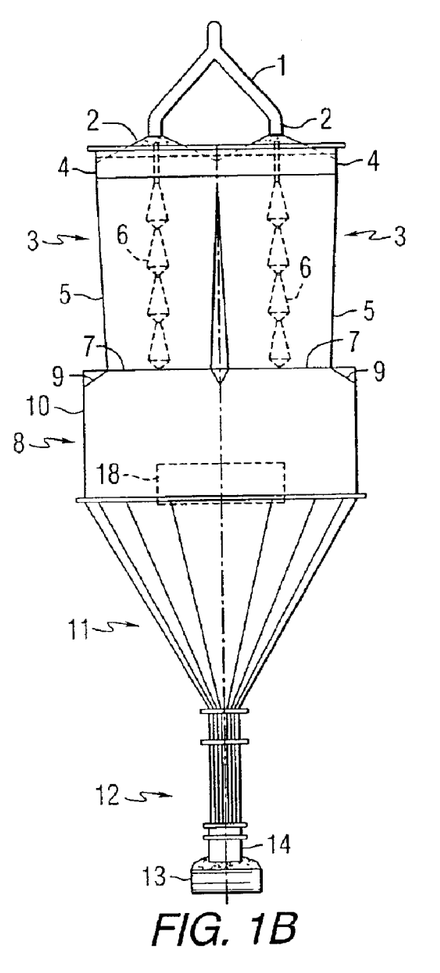
Figure 1C:
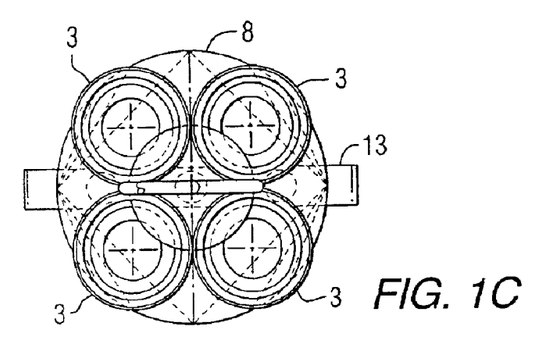

FIGS. 1A, 1B and 1C are front, side and top views of a curing vessel constructed in accordance with the present invention. A chute 1 or other means for introducing the particulate solids 2 continuously into the curing vessel is positioned at the top of the vessel. In the embodiment of FIGS. 1A, 1B and 1C, the upper curing unit includes four conical bins 3, each having a short vertical section 4 and a slightly converging frusto-conical portion, or cone 5. Alternatively, the curing vessel could be constructed using a single one of these bins. However, the use of multiple bins in parallel provides a greater curing capacity without using larger bins that might crush the particles. Central inserts 6 are positioned along a vertical axis of each bin. The addition of an insert 6 to each bin enhances the effectiveness of the vessel by slowing down the granular solids at the center of the bin so that the retention time in the vessel is more uniform. The insert 6 also provides inter-particle motion at the center whereas without the insert, the inter-particle motion may be insufficient to keep the particles from sticking. The outlet 7 of the bin provides the means for feeding the particulate solids to a larger diameter lower curing unit 8. Since the solids 9 exiting the upper bins have been partially cured, they can withstand the higher pressures associated with the larger lower curing unit 8. The lower curing unit 8 includes an intermediate section 10 and a hopper 11. The intermediate section 10 of the lower curing unit 8 can be a vertical cylinder or a slightly converging cone. Preferably, the outer shell of the intermediate section is a conical frustum with a convergence angle from top to bottom of no more than approximately 10 degrees from the vertical and where such angle θ, the top diameter D, and the flow rate Q are selected so that the slowest average volumetric strain rate VSR as given by:

$$VSR = 4\ \mathrm{TAN}(\theta) Q / (\pi D^3 / 4)$$

exceeds that required as determined experimentally to prevent the particles from sticking to each other.

The vertical section 4 of the upper curing unit has a height H that preferably does not exceed half of its diameter and the diameter times the bulk specific weight of the particulate solids does not exceed two times the bulk crush strength of the particulate solids. Preferably, the height H of the vertical section 4 or fill level in the vessel is such that γ H does not exceed the breaking strength of the granular particles, where γ is the bulk specific weight of the granular solid.

One or more inserts can be used to impose strain between particles flowing in the central core of the conical frustum and to slow down the normally faster flow in the conical frustum region. The inserts may also extend upward or downward or both along the axis of the vessel so as to form a conical shape. Preferably, the area of the insert in a horizontal plane, perpendicular to the solids flow direction, is between approximately 1% and 20% of the cross-sectional area of the conical frustum in a plane perpendicular to the direction of solids flow at the level of the insert.

A slight convergence is useful to limit crushing pressures on particles when the height of the upper portion exceeds half of its diameter. The curing vessel would need to be extremely high if a conical hopper were used. Instead of a cone, a much flatter one-dimensional converge race track cross-section hopper 11 is used to reduce the headroom. Multiple racetrack shaped one-dimensional convergent hoppers 12 are used to further reduce headroom. The multiple hoppers feed a receiving belt conveyor 13. Adjustable cylinders 14 can be used to control the outflow of particulates to the belt 13 and add layers 15, 16, and 17 upon each other. The cylinders also provide a quick adjustment for reversing the belt direction simply by changing the relative heights of the outside cylinders 15 and 17 so as to reverse the height of the layers 15 and 17. The relative layered depths 15, 16, and 17 can also be adjusted to fine tune the inter-particle motion in the vessel.

In the vessel of FIGS. 1A, 1B and 1C, the converging outer shell of the hopper can be comprised of racetrack shaped cross-sections arranged such that convergence occurs only in one direction at a time with the walls of the converging portion of the vessel steep being enough to produce flow adjacent to the walls and a nearly uniform flow velocity across the cross-section.

The inter-particle motion in the converging sections of the hopper is generally provided by the convergence. The inter-particle motion of the particulates in the cylindrical or steep walled intermediate section 10 of the lower curing unit is provided by a flow adjusting insert in the form of an inner-hollow cylinder 18.

The lower curing unit and insert can be arranged so as to produce flow at the converging walls around the insert where such flow extends both above and below said insert. Preferably, the horizontal distance between the converging walls and the insert is approximately half the width of the insert in the horizontal direction perpendicular to the axis of the hopper.

The insert extends upward or downward or both in a racetrack shaped cross-section with a continually decreasing cross-sectional area. Preferably, the top most extension of the insert exceeds the height of the upper hopper section and/or the extension downward protrudes into the lower hopper section. The extension of the insert upward or downward may have essentially vertical sides in regions where the hopper has essentially vertical or slightly diverging sides, and where the lower extension has a sloping section that is steeper than the upper hopper portion of the one-dimensional convergence hopper and less steep than the lower portion of the one-dimensional convergence hopper, and where both slopes are greater than the angle of repose of the particulates The insert 18 serves as means for introducing shear in the intermediate vertical section, and preferably extends above the juncture of the converging and vertical section and is adjustable vertically so as to allow the lower edge of the cylinder to extend below the junction of the upper cylinder and the converging sections. The cylinder can be adjusted to provide a somewhat faster but controlled flow in the center of the vessel as well as varying flow velocities in the annular region around the cylinder and between the converging vessel walls. The cylinder can be placed low enough to cause sufficient differential velocities in the flowing material so as to produce a blending of material.

A lower converging section of the hopper 11 can comprise a multiple outlet one-dimensional racetrack cross-section formed at the top of a lower converging section, a single elongated race track divided into two or more hoppers that first transition to a less elongated race track and then to a circle, or an even less elongated race track less than that at the top.

The required shear to prevent particle sticking can be accomplished by regulating the feed rate from the multiple outlets so as to produce the required shear strain between particles. Alternatively, the shear strain can be caused by a racetrack shaped insert in the upper converging racetrack section, with the insert lying essentially perpendicular to the axis of the upper converging section.

Figure 2A:
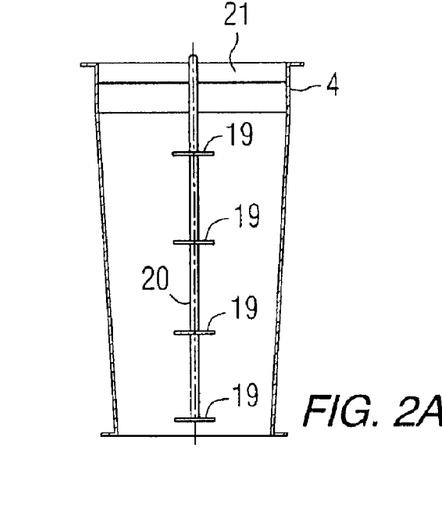
FIGS. 2A, 2B, 2C, 2D and 2E are various views of a conical shaped upper curing unit of the curing vessel.
Figure 2B:
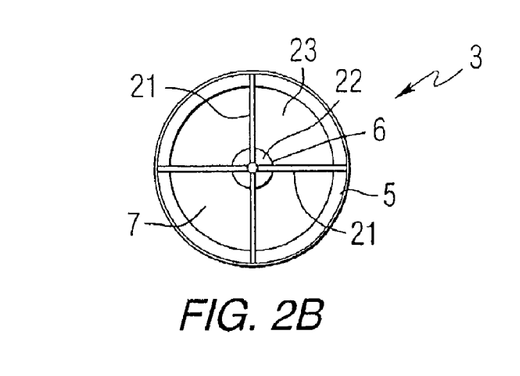
Figures 2C, 2E:
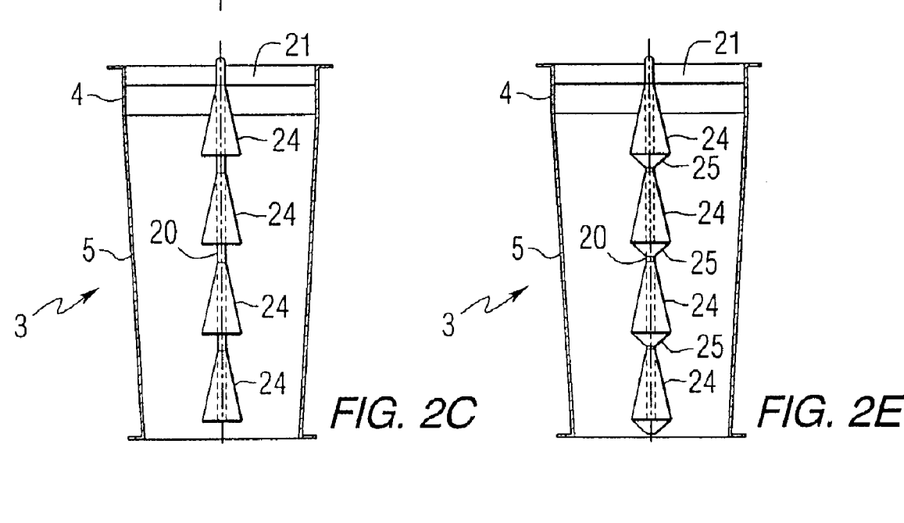
Figure 2D:
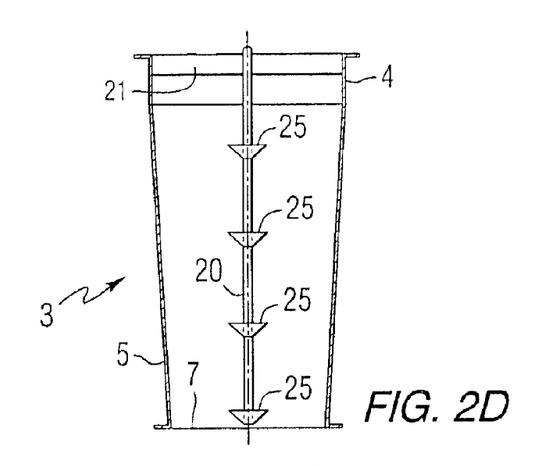

FIGS. 2A, 2B, 2C, 2D and 2E are various views of the conical shaped upper curing unit of the curing vessel. A basic insert shown in FIG. 2A comprises a plurality of flat plates 19 arranged on support rod 20, held in place by a support 21. The cross-sectional area of the plates must be sufficient to influence the solids flowing around it. This requires a cross-sectional area 22 (see FIG. 2B) that is between 1% and 20% of the total cross-sectional area 23 (see FIG. 2B) of the conical section in a plane perpendicular to the direction of solids flow at the level of the insert. FIG. 2C shows the addition of cones 24 to the insert, with the cones being oriented to point in a direction opposite the direction of flow of the solids. This prevents buildup of solids on the insert and more clearly defines the region of shear imposed by the insert. The cone also may extend the region of influence upward from a flat plate further than if solids were allowed to build up on the plates 19. FIG. 2D shows the addition of cones 25 extending below the flat plates. This defines the flow channels and spheres of influence below the plates more precisely than the angle of repose of the particulate solids. FIG. 2E shows the inserts with cones 24 and 25 extending both upward and downward. The upper curing unit can have a retention time sufficient to cure the particulates to a breaking strength sufficient to withstand the larger pressures of the larger lower vessel.

Figure 3A:
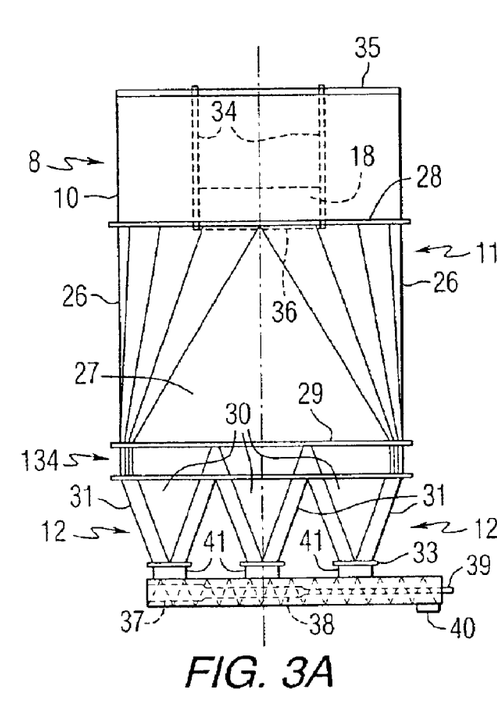
FIGS. 3A, 3B and 3C are front, top and side views of an embodiment of the lower curing unit with multiple outlets.
Figure 3B:
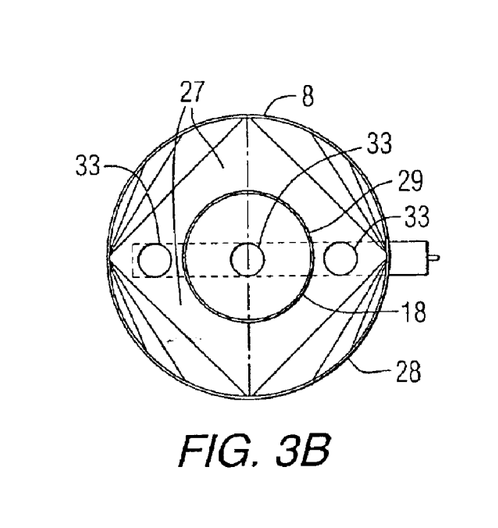
Figure 3C:
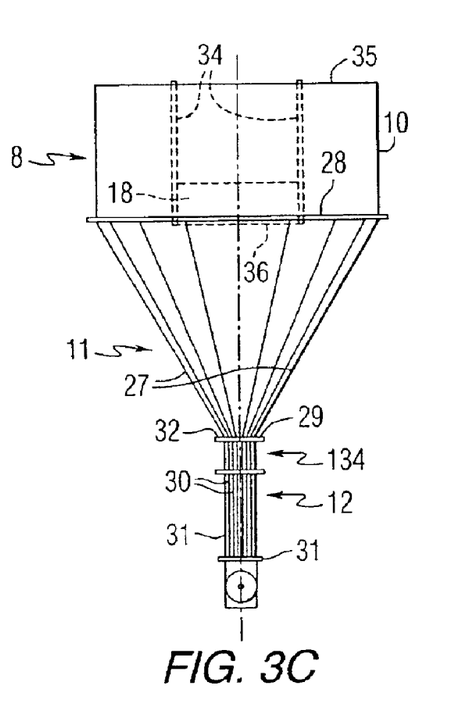

FIGS. 3A, 3B and 3C are front, top and side views of the lower curing unit 8 with multiple outlets. A one-dimensional convergence racetrack shaped cross-section hopper 11, includes end walls 26 making up the circular part of the racetrack that are vertical or slightly diverging downward with the flat sidewalls 27 converging downward. The hopper horizontal cross-section changes continually from a circular racetrack shape 28 at the top of hopper 11 to the combination of straight sides with circular end sections of a racetrack shape 29. Multiple additional hoppers 12 have vertical or slightly diverging downward flat sidewalls 30 with the circular end walls 31 converging downward. The cross-section changes continuously from the straight-sided circular ended type racetrack 29 to a circular racetrack 33 at the bottom. A transition piece 134 connects the elongated oval-shaped racetrack 29 of the first hopper 11 to the individual oval shaped racetrack sections of the upper parts of the lower hoppers 12. The racetrack cross-sections of the transition pieces 134 have quarter circular racetrack sections connected to straight sections.

The vessel of FIGS. 3A, 3B and 3C includes multiple outlets wherein the means for removing material includes multiple adjustable vertical cylinders ending at various heights above a belt feeder. The cylinder heights increase in the direction of belt movement so as to place one layer of particulates on top of another. The cylinders can be adjustable vertically so as to allow reversal of the belt direction and still provide flow from each of the multiple outlets. Also, the vertical cylinders may be adjusted so as to regulate the particulate flow velocity in the hopper above it and thus control the inter-particle motion between particulates and/or control the relative retention time in the vessel so as to cause blending of the particulates.

A screw feeder 39 can serve as means for removing particulates from the vessel. A screw feeder with varying shaft diameters can define the removal rate from each of the outlets. Preferably, the pitch of the screw is constant and uniformity of flow velocity at the outlets of the hopper is achieved by a vertical section between the screw inlet and the hopper outlet.

A hollow cylinder 18 with support rods 34 supported by the top 35 of the vessel can be adjusted so that the lower edge 36 of the cylinder 18 lies below the circular racetrack 28 of the first racetrack shaped hopper 11. This produces a faster moving central flow channel with somewhat slower flow near the vertical end walls 26 of the hopper 11 and an even slower flow between the hollow cylinder 18 and upper vessel side walls 26 of the hopper 11. This causes the inter-particle motion necessary to prevent sticking of the particulates. If more inter-particle motion is required to prevent sticking of the particulates or if some degree of blending in time is desired, the cylinder 18 can be adjusted downward by support rods 34. A screw feeder with varying capacities under each hopper outlet is used to extract the solids from the hoppers. Varying shaft diameters 37, 38, and 39, which decrease toward the outlet 40, can provide the required change of screw capacity. The vertical sections 41 between the screw and the hopper outlet 33 provide a uniform velocity at the hopper outlet 33.

Figure 4A:
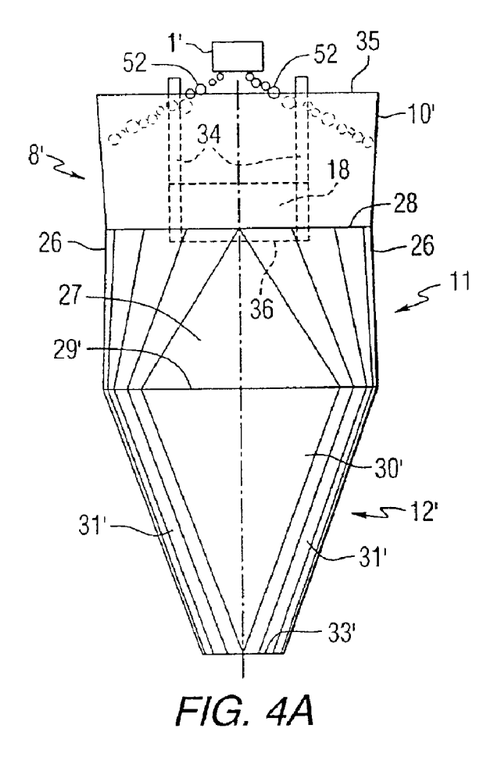
FIGS. 4A, 4B and 4C are front, top and side views of the one-dimensional racetrack shaped cross-section curing unit hopper with a single outlet.
Figure 4B:
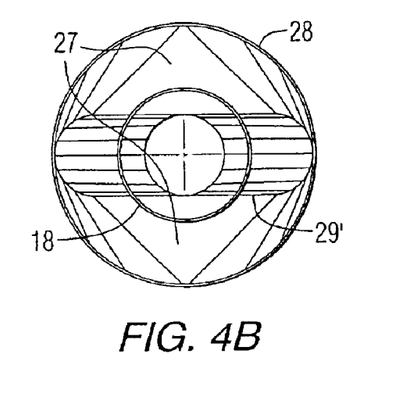
Figure 4C:
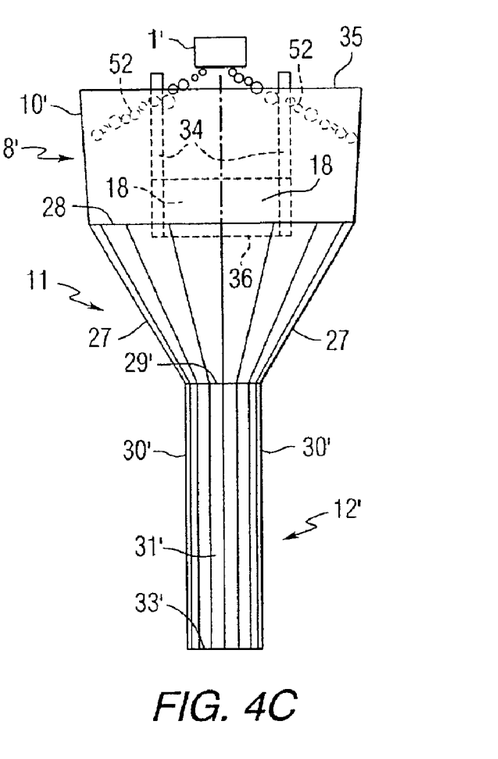

FIGS. 4A, 4B and 4C show a single outlet one-dimensional convergence racetrack shaped cross-sectional hopper 8'. FIGS. 4A, 4B and 4C are the front, top and side views, respectively, of this hopper. This configuration has the advantage of using a single outlet and a much smaller feeder. In the case shown, a single inlet chute 1' is used to place particulates 52 into the vessel 8'. The height of the vertical section 10' must be such that it does not cause the granules to crush. If this section 10' is a slightly downward converging cone (0.5 degrees is sufficient in many cases), the bulk crushing strength of the particulates must exceed $\gamma D/2$ by the time the particulates reach the top 28' of the one-dimensional convergent hopper 11'. $\gamma$ is the bulk density of the particulates and D is the top diameter of the upper section 10'. If the vertical section 10' is a cylinder or a slightly diverging cone, the bulk crushing strength of the granules must exceed $\gamma$ times the average height of the material in section 10' by the time the material reaches the top 28' of hopper 11'. The end walls 26' of the hopper 11' are vertical or diverging slightly downward while the sidewalls 27' converge to the racetrack shape 29'. The lower hopper 12' has side walls 30' vertical or diverging slightly downward, while end walls 31' converge to a circular cross-section 33'. In some cases where minimizing headroom is of the essence, the lower portion of hopper 12' can be cut off at a level with an oval cross-section and a larger feeder can be used at this position to remove the particulates.

The bottom 36 of hollow cylinder 18 is shown significantly lower than in FIG. 3. This lower position of the cylinder will provide blending with time, thus causing an homogenizing of upstream process variations.

Figure 5A:
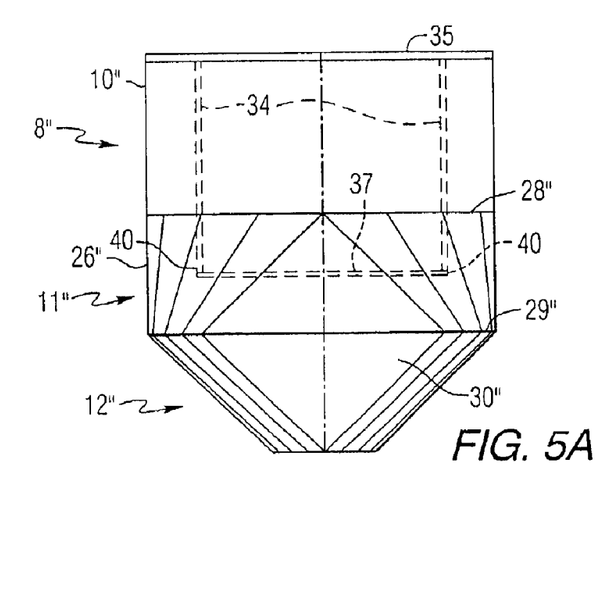
FIGS. 5A, 5B and 5C are front, top and side views of the upper portion of the one-dimensional convergence racetrack shaped hopper including a flow adjusting insert.
Figure 5B:
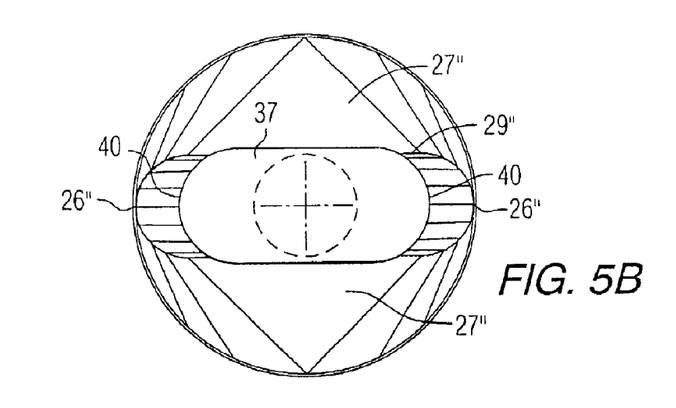
Figure 5C:
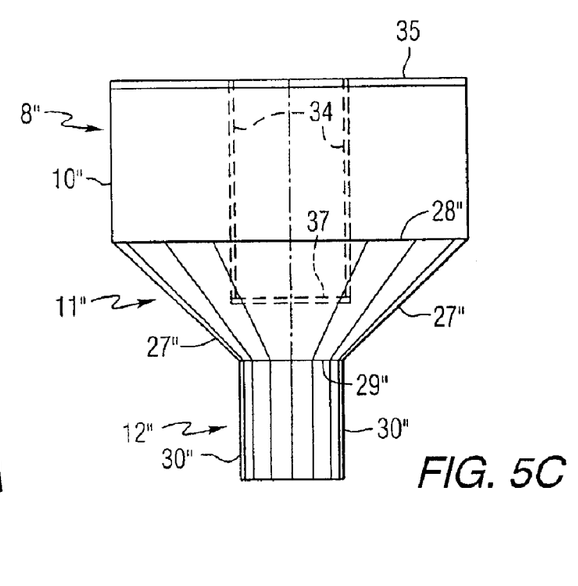

FIGS. 5A, 5B and 5C shows a curing vessel 8" with a single outlet one-dimensional racetrack cross-section hopper 11" with a single outlet lower hopper 12" that is equipped with an insert 37 which allows a much flatter angles in the hopper and thus saves headroom and associated costs. Except for the angles, the features of the hopper sections 11" and 12" are the same as in FIGS. 4A, 4B and 4C. The insert 37 is supported on rods 34 the same as the hollow cylinder 12" in FIGS. 1A, 1B and 1C and FIGS. 3A, 3B and 3C. In this case, the insert is a flat plate 37 and does not allow material to pass through it. The insert 37 is racetrack shaped. The width of the racetrack, as evident in FIG. 5C, is approximately half the horizontal distance between the slopping walls 27" of hopper 11" at the elevation of the insert. The distance between the oval ends 40 of the insert 37 and the slightly diverging end wall 26" of hopper 11" is approximately equal to half the width of the oval 29" between hopper sections 11" and 12". This distance is the same as the distance between flat plates 30" in FIG. 5C. The insert 37 provides a slowing of the particulate flow in the center of vessel 8" as well as provides the necessary interparticle motion between the particulates in vessel 8". The insert can be moved up and down on support rods 34 to optimize both the interparticle motion and the uniformity of retention time in vessel 8".

Figure 6A:
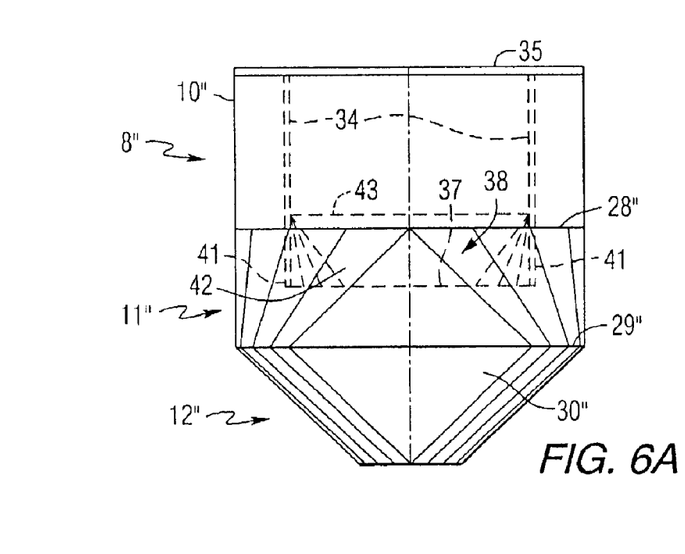
FIGS. 6A, 6B and 6C are front, top and side views of the upper portion of the hopper showing the insert extending upward.
Figure 6B:
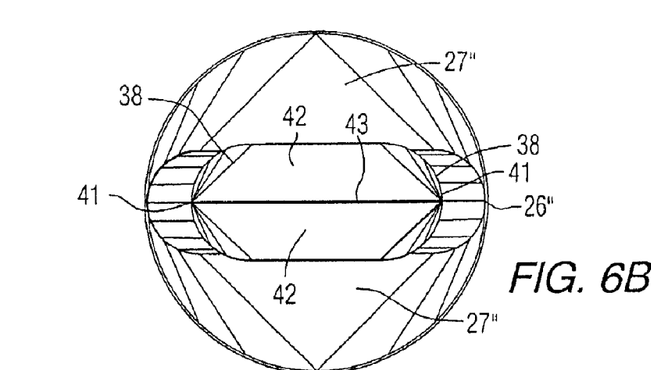
Figure 6C:
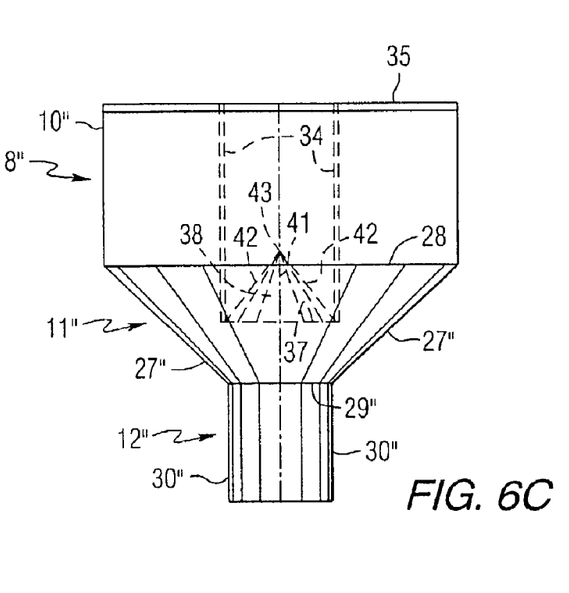

FIGS. 6A, 6B and 6C show the same vessel and insert as in FIGS. 5A, 5B and 5C except the insert 37 includes an upward extension 38 comprising a series of racetrack shapes stacked to a top line 43. The top line 43 generally lies above the intersection 28" of the upper cylinder or cone 10" and the hopper 11". The end walls 41 of the insert are essentially vertical while the side plates 42 form a converging channel with the side plates 27" of hopper 11". In this way, the flow channel formed by the insert approximates a one-dimensional convergence. The advantage of the insert extension upward is that the flow channel formed is positively defined by the insert as opposed to the particulate defined shape that is free to form on the flat plate. This assures that interparticle motion of the particulates extends upward into the cylinder 10", and assures flow at the walls of hopper 11".

Figure 7A:
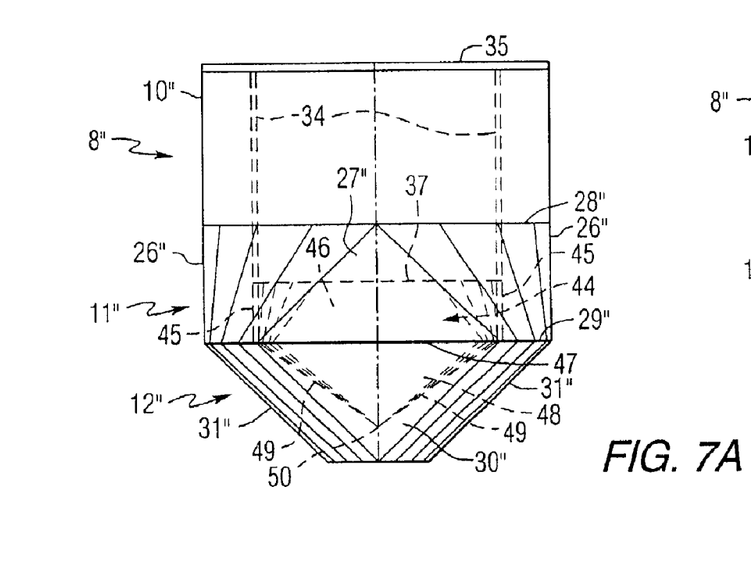
FIGS. 7A, 7B and 7C are front, top and side views of the upper portion of the hopper showing the insert extending downward.
Figure 7B:
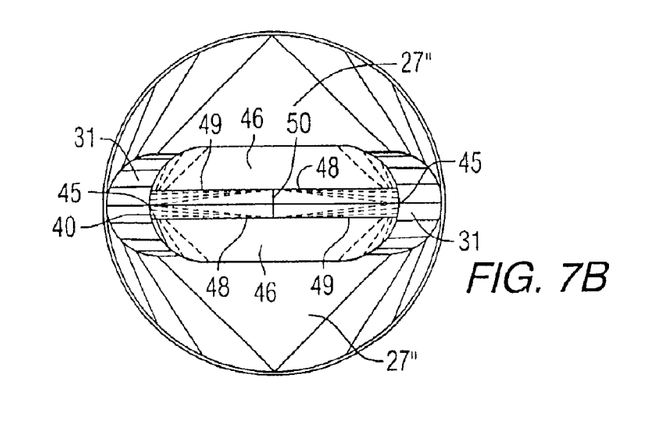
Figure 7C:
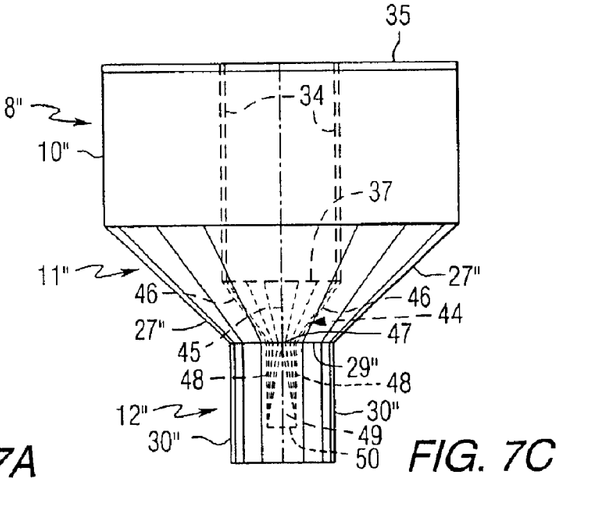

FIGS. 7A, 7B and 7C shows a similar insert to that of FIGS. 5A, 5B and 5C with a downward extension 44 comprising a plurality of racetrack shapes that compliment the shape of the hopper. The end walls 45 of the extension 44 are essentially vertical while the side walls 46 form an angle somewhat steeper than the hopper walls 27" of hopper 11". This one-dimensional convergence shape compliments the shape of hopper 11". As the extension continues downward, the insert shape changes so as to complement the shape of hopper 12". The transition 47 between these two shapes is generally at or above the transition 29" of hoppers 11" and 12". The racetrack configuration continues below the transition 47 with essentially vertical flat plates 48 and curved end walls 49 that extend to a lower line 50. Walls 49 are generally less steep than the converging walls 31" of the hopper 12" but steeper than the angle of repose of the particulates. By extending the insert downward, the insert walls influence the flow of the particulates at the walls of hoppers 11" and 12". Without the insert extension, the flow is determined only by the angle of repose of the particulates below the flat insert.

Figures 8A, 8B:
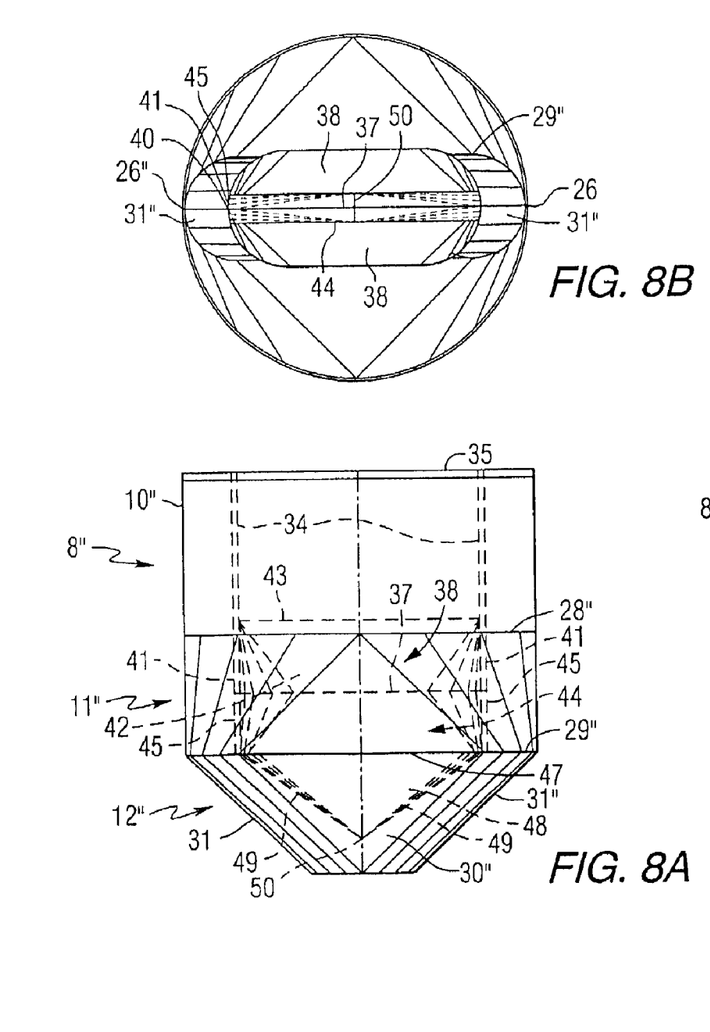
FIGS. 8A, 8B and 8C are front, top and side views of the upper portion of the hopper showing the insert extending both upward and upward.
Figure 8C:
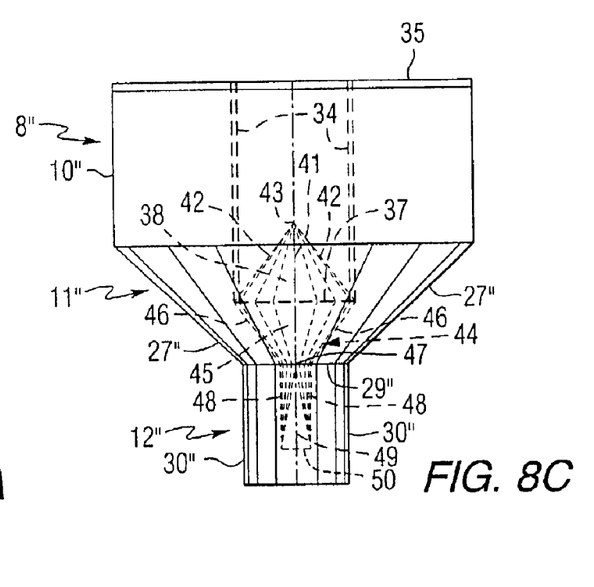

FIGS. 8A, 8B and 8C show the same hopper and insert as FIGS. 5A, 5B and 5C with the insert extending both upward and downward. This achieves the advantages of both the upward and downward extensions of the insert as described in FIGS. 6A, 6B and 6C and FIG. 7B.

Figure 9A:
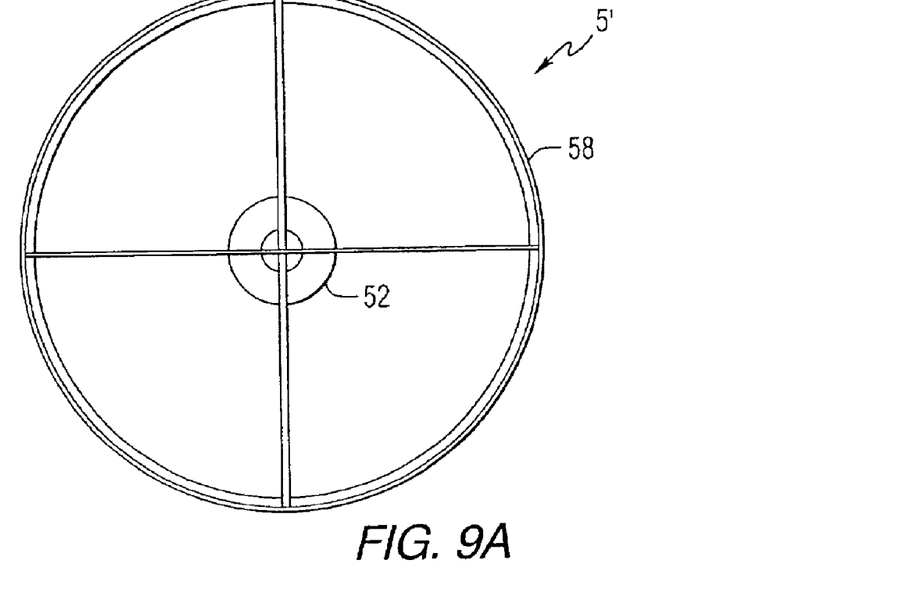
FIGS. 9A and 9B are top and side views of an alternative conical and cylindrical shaped curing unit and associated insert.
Figure 9B:
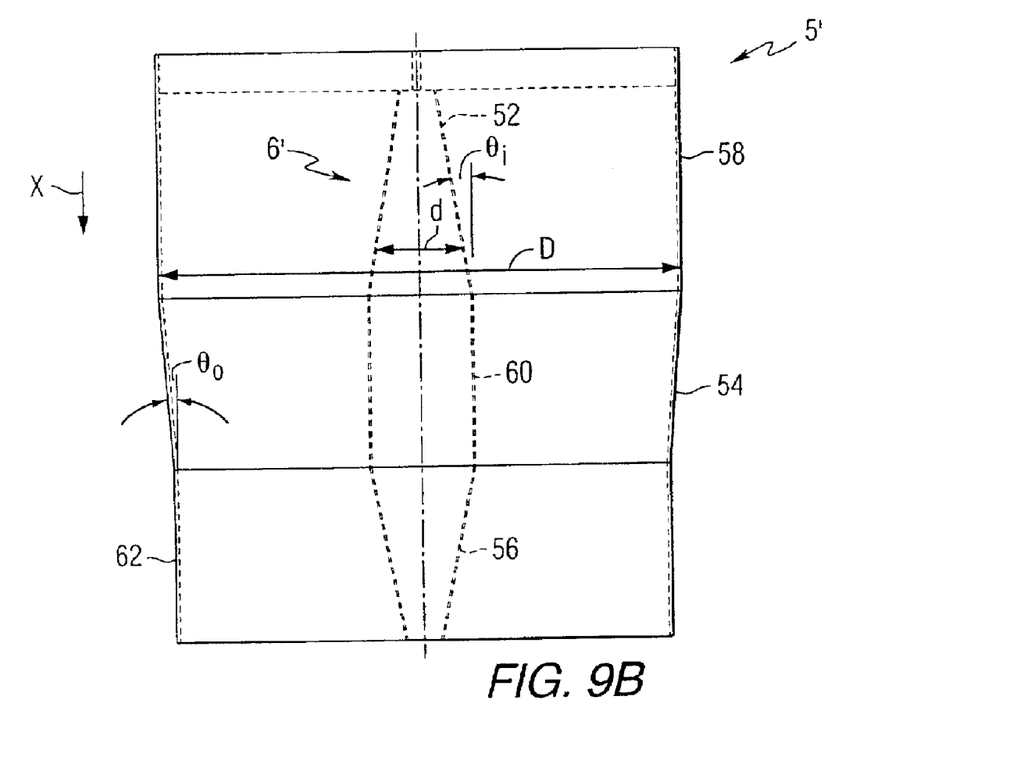

The headroom required for the upper conical curing vessel can be minimized by using various combinations of cones 52, 54, 56 and cylinders 58, 60, 62 in both the outer vessel 5' and the associated insert 6' as shown in FIGS. 9A, and 9B. The vertical section can be more extensive than in FIG. 2 by using the convergence produced by the conical portions of the insert 6' to produce the necessary volumetric strain rate VSR.

$$VSR = (dA/dX)Q/A^2$$

where A is the cross-sectional area between the insert and the outer vessel, X is the vertical direction and Q is the volumetric flow rate. Specifically, in the configuration of FIGS. 9A and 9B, $$VSR = 16(D(\tan \theta_0) - d(\tan \theta_i))Q/(\pi(D^2-d^2)(D^2-d^2))$$

where D is the inside diameter of the outer vessel, d is the outside diameter of the insert, $\theta_0$ is the angle of the outer vessel wall measured from the vertical with positive inclined toward the insert, $\theta_i$ is the angle of the insert surface measured from the vertical with positive inclined toward the vessel.

In the upper portion of the vessel in FIGS. 9A and 9B, the angle $\theta_0$ is zero and the VSR is zero unless d is positive. Since VSR of zero is not acceptable it is necessary that d be non-zero at the top of the material in the vessel. Since VSR must occur throughout the vessel it is necessary for the vessel walls to converge in the region where the insert is a cylinder. In the lowest extremity of the vessel, the vessel walls are vertical and the VSR is achieved by the decrease of the insert diameter d. This divergence of the area 'A' causes an increased solids contact pressure on the particles. This is acceptable since the particles are partially cured at this position and can withstand the greater pressure.

In the upper vessel, the headroom can be optimized by arranging the vessel and insert walls in a series of cones and cylinders so as to maximize the volume in a given height while still providing the required VSR and limiting the solids contact pressure to the granular breaking pressure at the particular stage of curing. This means a low pressure and high VSR in the initial stages with an allowable decrease in VSR and allowable increase in the solids contact pressure as the curing progresses lower in the vessel. This is illustrated by the different upper and lower vessel designs and in the choice of vessel and insert shape in the alternate upper vessel in FIGS. 9A and 9B.

Figure 10A:
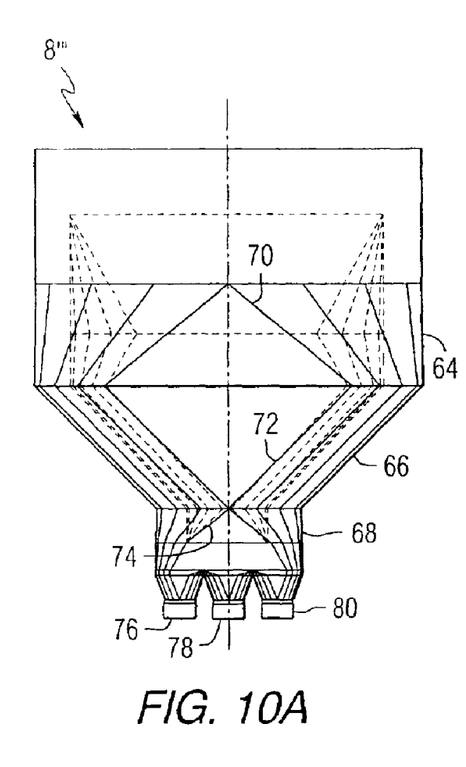
FIGS. 10A, 10B, and 10C, are front, top and side views of a curing vessel including multiple features of the invention in combination.
Figure 10B:
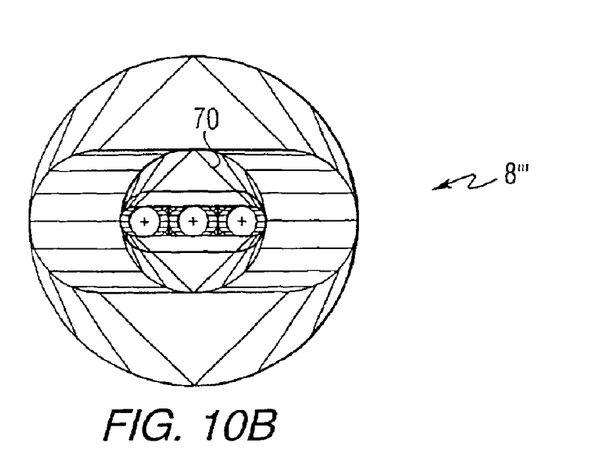
Figure 10C:
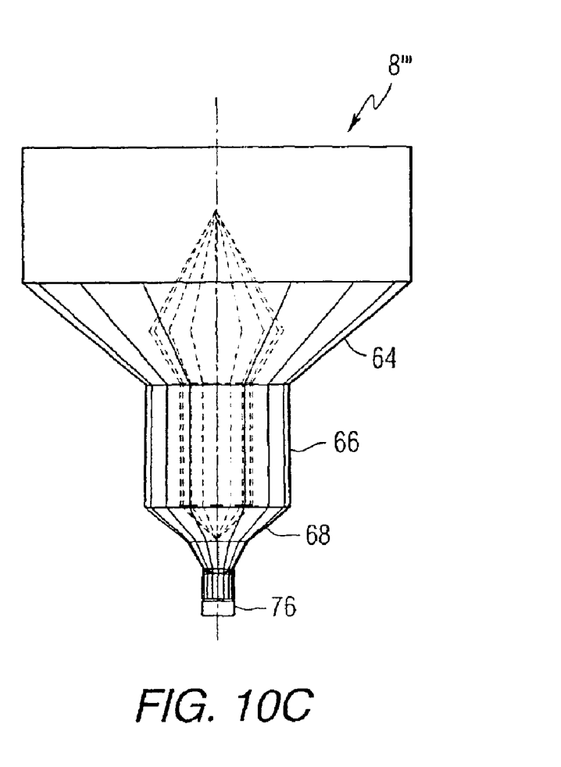

The lower vessel 8''' as shown in the FIGS. 10A, 10B, and 10C is comprised of multiple racetrack configurations 64, 66, 68, racetrack interior inserts 70, 72, 74 and multiple outlets 76, 78, 80 so as to minimize the required headroom, while still maintaining the required VSR to keep the particles from sticking and maintaining the pressures below the crushing strength of the particles.

The invention provides a bulk solids vessel comprising an essentially vertical upper and converging lower section that limits solids contact pressure on the bulk granular solid passing through it to less than the bulk crushing pressure of the granules and provides a means for introducing interparticle motion sufficient to prevent the granules from sticking to each another.

The invention can further provide a vessel as described above further comprising an outer shell, wherein the outer shell is a conical frustum with a convergence angle from top to bottom of no more than approximately 10 degrees from the vertical and where such angle θ, the top diameter D, and the flow rate Q are selected so that the slowest average volumetric strain rate VSR as given by VSR=4 TAN (θ) Q/(πD³/4) exceeds that required as determined experimentally to prevent the granules from sticking to each other.

The invention can also provide a vessel and insert each comprised of conical frustum and cylindrical sections such that the vessel inside diameter D, the angle of the vessel $\theta_0$, the outside diameter of the insert d, the angle of the insert $\theta_i$ and the volumetric flow rate Q at any level are arranged such the average volumetric strain rate VSR as given by:

$$VSR=16(D(\tan \theta_0)-d(\tan \theta_i))Q/(\pi(D^2-d^2)(D^2-d^2))$$

exceeds that required to keep the particles from sticking.

The present invention can further provide a vessel and insert each comprising racetrack shaped cross-sections such that the vessel forms a series of vertical and converging sections that converge in one dimension only such that the average volumetric strain rate VSR necessary to keep particles from sticking is given by $$VSR=(dA/dX)Q/A^2$$

While particular embodiments of this invention have been described above for purposes of illustration, it will be evident to those skilled in the art that numerous variations of the described embodiments may be made without departing from the scope of the invention as defined by the following claims.

What is claimed is:

1. A bulk granular solids gravity flow curing vessel comprising:
    an upper curing unit having a top opening for receiving particulate solids;
    a lower curing unit coupled to receive particulate solids from the upper curing unit; and
    at least one of the upper and lower curing units including a first intermediate section having substantially vertical sidewalls, a first hopper positioned to receive the particulate solids from the intermediate section, and a first velocity adjustment means positioned in the intermediate section and/or the first hopper.

2. A bulk granular solids gravity flow curing vessel according to claim 1, wherein the first one of the upper and lower curing units comprises:
    a conical bin; and
    wherein the first velocity adjustment means comprises a central insert positioned along a central axis of the bin.

3. A bulk granular solids gravity flow curing vessel according to claim 2, wherein the central insert comprises:
    a rod positioned along the central axis of the bin; and
    a plurality of plates spaced along the rod and lying in planes that are perpendicular to the axis.

4. A bulk granular solids gravity flow curing vessel according to claim 3, wherein the central insert further comprises:
    a plurality of cones and cylinders, each of the cones and cylinders having a base positioned adjacent to one of the plates.

5. A bulk granular solids gravity flow curing vessel according to claim 1, wherein the second one of the upper and lower curing units includes:
    a second intermediate section having substantially vertical sidewalls, a second hopper positioned to receive the particulate solids from the intermediate section, and a second velocity adjustment means positioned in the intermediate section and/or the first hopper.

6. A bulk granular solids gravity flow curing vessel according to claim 5, wherein the second velocity adjustment insert comprises:
    a hollow cylinder.

7. A bulk granular solids gravity flow curing vessel according to claim 6, wherein the hollow cylinder is positioned to extend into the second hopper.

8. A bulk granular solids gravity flow curing vessel according to claim 5, wherein the diameter of the hollow cylinder is approximately one half of the diameter of the second intermediate section.

9. A bulk granular solids gravity flow curing vessel according to claim 5, wherein the second velocity adjustment insert comprises:
    a horizontal flat plat.

10. A bulk granular solids gravity flow curing vessel according to claim 9, wherein the second velocity adjustment insert comprises:
    an upper extension.

11. A bulk granular solids gravity flow curing vessel according to claim 9, wherein the second velocity adjustment insert further comprises:
    a lower extension.

12. A bulk granular solids gravity flow curing vessel according to claim 1, wherein the upper curing unit comprises a conical section having a convergence angle of less than 10 degrees from vertical.

13. A bulk granular solids gravity flow curing vessel according to claim 1, wherein the upper curing unit comprises:
    a plurality of conical sections.

14. A bulk granular solids gravity flow curing vessel according to claim 1, wherein the first hopper comprises a one-dimensional converge racetrack hopper.

15. A bulk granular solids gravity flow curing vessel according to claim 14, wherein the second velocity adjustment insert comprises:
    a racetrack shaped insert.

16. A bulk granular solids gravity flow curing vessel according to claim 15, wherein the racetrack shaped insert extends into a substantially vertical sidewall section and into the racetrack shaped hopper.

17. A bulk granular solids gravity flow curing vessel according to claim 1, wherein the velocity adjustment means and a combination of outer walls and insert walls are selected so that a smallest average volumetric strain rate VSR as given by:

$$VSR=(dA/dX)Q/A^2$$

exceeds that required as determined experimentally to prevent the particles from sticking to each other.

18. A bulk granular solids gravity flow curing vessel according to claim 14, further comprising:
    a plurality of additional one-dimensional converge racetrack hoppers coupled to the first hopper.

19. A bulk granular solids gravity flow curing vessel according to claim 18, further comprising:
    a plurality of vertically adjustable cylinders, each of the cylinders coupled to one of the one-dimensional converge racetrack hoppers.

20. A bulk granular solids gravity flow curing vessel according to claim 1, wherein the upper curing unit comprises:

a conical frustum having a convergence angle from top to bottom of no more than 10 degrees from vertical and where the convergence angle θ, a top diameter D of the conical frustum, and a flow rate Q are selected so that a slowest average volumetric strain rate VSR as given by:

$$VSR = 4\ TAN(\theta) Q/(\pi D^3/4)$$

exceeds that required as determined experimentally to prevent the particles from sticking to each other.

21. A bulk granular solids gravity flow curing vessel according to claim 1, wherein the height of the intermediate section is less than one half of its diameter and the diameter times the bulk specific weight of the particulate solids does not exceed two times the bulk crush strength of the particulate solids.

22. A bulk granular solids gravity flow curing vessel according to claim 1, wherein the first hopper comprises:
   a plurality of racetrack shaped cross-sections arranged such that convergence of the particulate solids occurs only in one direction.

23. A bulk granular solids gravity flow curing vessel according to claim 1, further comprising:
   a plurality of outlets each including means for adjusting relative particulate velocities to produce inter-particulate motion and/or blending.

24. A bulk granular solids gravity flow curing vessel comprising:
   a first section having substantially vertical sidewalls;
   a first hopper positioned to receive particulate solids from the first section; and
   a first velocity adjustment means positioned in the first section, wherein the first velocity adjustment means comprises a hollow cylinder.

25. A bulk granular solids gravity flow curing vessel according to claim 24, wherein the hollow cylinder is positioned to extend into the first hopper.

26. A bulk granular solids gravity flow curing vessel according to claim 25, wherein the diameter of the hollow cylinder is approximately one half of the diameter of the first section.

27. A bulk granular solids gravity flow curing vessel according to claim 24, wherein the first velocity adjustment means comprises:
   a horizontal flat plate.

28. A bulk granular solids gravity flow curing vessel according to claim 27, wherein the first velocity adjustment means further comprises:
   an upper extension.

29. A bulk granular solids gravity flow curing vessel according to claim 27, wherein the first velocity adjustment means further comprises:
   a lower extension.

30. A bulk granular solids gravity flow curing vessel according to claim 24, wherein the first hopper comprises a one-dimensional converge racetrack hopper.

31. A bulk granular solids gravity flow curing vessel comprising:
   a first section having substantially vertical sidewalls;
   a first hopper positioned to receive particulate solids from the first section; and
   a first velocity adjustment means positioned in the first section; and
   a plurality of additional one-dimensional converge racetrack hoppers coupled to the first hopper.

32. A bulk granular solids gravity flow curing vessel according to claim 31, further comprising:
   a plurality of vertically adjustable cylinders, each of the cylinders coupled to one of the one-dimensional converge racetrack hoppers.

33. A bulk granular solids gravity flow curing vessel according to claim 24, wherein the height of the intermediate section is less than one half of its diameter and the diameter times the bulk specific weight of the particulate solids does not exceed two times the bulk crush strength of the particulate solids.

34. A bulk granular solids gravity flow curing vessel comprising:
   a first section having substantially vertical sidewalls;
   a first hopper positioned to receive particulate solids from the first section; and
   a first velocity adjustment means positioned in the first section; and
   wherein the first hopper comprises a plurality of racetrack shaped cross-sections arranged such that convergence of the particulate solids occurs only in one direction.

35. A bulk granular solids gravity flow curing vessel comprising:
   a first section having substantially vertical sidewalls;
   a first hopper positioned to receive particulate solids from the first section; and
   a first velocity adjustment means positioned in the first section; and
   a plurality of outlets each including means for adjusting relative particulate velocities to produce inter-particulate motion and/or blending.

36. A bulk granular solids gravity flow curing vessel comprising:
   a first section having substantially vertical sidewalls;
   a first velocity adjustment means positioned in the first section and having non-vertical sidewalls;
   a second section having non-vertical sidewalls and positioned to receive particulate solids from the first section; and
   a second velocity adjustment means positioned in the second section and having substantially vertical sidewalls.

37. A bulk granular solids gravity flow curing vessel according to claim 36, further comprising:
   a third section having substantially vertical sidewalls and positioned to receive particulate solids from the second section; and
   a third velocity adjustment means positioned in the third section and having non-vertical sidewalls.

38. A bulk granular solids gravity flow curing vessel according to claim 36, wherein:
   the first section, the first velocity adjustment means, the second section having non-vertical sidewalls, and the second velocity adjustment means are positioned on a common axis; and
   the first section and the second velocity adjustment means comprise cylinders, and the second section and the first velocity adjustment means comprise cones.

39. A bulk granular solids gravity flow curing vessel according to claim 36, wherein:
   a sidewall of the first section forms an angle $\theta_0$ with respect to a vertical direction, and a sidewall of the first velocity adjustment means forms an angle $\theta_i$ with respect to the vertical direction such that the average volumetric strain rate VSR for particulate solids in the vessel is given by:

$$VSR = 16(D(\tan\theta_o) - d(\tan\theta_i))Q/(\pi(D^2-d^2)(D^2-d^2))$$

where D is the inside diameter of the first section, d is the outside diameter of the first velocity adjustment means, and Q is volumetric flow rate of the particulate solids.

* * * * *